United States Patent [19]

Singh et al.

[11] Patent Number: 5,876,751

[45] Date of Patent: Mar. 2, 1999

[54] ANTISPASMODIC AND ANTINFLAMMATORY COMPOSITION AND A PROCESS FOR THE MANUFACTURE THEREOF

[75] Inventors: Amarjit Singh, Chandigarh; Rajesh Jain, New Delhi, both of India

[73] Assignee: Panacea Biotec Limited, New Delhi, India

[21] Appl. No.: 824,409

[22] Filed: Mar. 26, 1997

[30] Foreign Application Priority Data

Apr. 12, 1996 [IN] India ......................................... 792/96

[51] Int. Cl.$^6$ ...................................................... A61K 9/20
[52] U.S. Cl. .......................... 424/464; 424/456; 424/468; 424/489; 514/962
[58] Field of Search ..................................... 424/464, 456, 424/468, 489; 514/962

[56] References Cited

U.S. PATENT DOCUMENTS 5,446,070   8/1995   Mantelle .

FOREIGN PATENT DOCUMENTS 261585        1/1990   Canada .
WO 93/00895   1/1993   WIPO .

OTHER PUBLICATIONS

Dureng et al, Relative Efficacies of some Antispasmodic Drugs on the Digestive Tract and Bladder of the Anestetized Dog, J. Pharmacol., 12(2), 131–145, Jan. 1981.

*Primary Examiner*—Thurman K. Pace
*Assistant Examiner*—Brian K. Seidleck
*Attorney, Agent, or Firm*—Oblon, Spivak, McClelland, Maier & Neustadt, P.C.

[57] ABSTRACT

A composition comprising at least one non-steroidal antiinflammatory drug, their salts, their chirally pure forms, isomers and derivatives, analogues and adducts thereof and two drugs pitofenone hydrochloride and fenpiverinium bromide in a pharmaceutically acceptable combination.

10 Claims, No Drawings

ANTISPASMODIC AND ANTINFLAMMATORY COMPOSITION AND A PROCESS FOR THE MANUFACTURE THEREOF

BACKGROUND OF THE INVENTION

1. Field of the Invention

The present invention describes a novel composition comprising a nonsteroidal antiinflammatory drug, their salts, their chirally pure forms, isomers and derivatives, analogues and adducts thereof and two drugs pitofenone hydrochloride and fenpiverinium bromide in a pharmaceutically acceptable combination for use in mammals particularly human beings.

2. Description of the Background

Amongst the various non-steroidal antiinflammatory drugs diclofenac particularly sodium diclofenac is widely used in the treatment of rheumatoid arthritis, osteoarthirities and ankylosing spondylitis. This has been disclosed in the following references (references from U.S. Pat. No. 5,202, 159).

As such, intestinal, ureteric and biliary colic are extremely common clinical conditions requiring prompt medical attention to relieve the symptoms and help the patient get back to his/her vocation to avoid/minimize economic loss and reduce the load on the medical institution. Non surgical treatment can provide immediate relief to the patient while investigations are being carried out to determine the future course of management. Currently available treatment modalities include anticholinergics like, atropine and its derivatives, ambutonium, glycopyrronium, isoperopamide, pripenzolate, etc. Combination therapy with analgin, pitofenone and fenpiverinium are also used. In addition, drugs such as meberverine valethamate bromide, clidinium are also used with.

All drugs do not provide predictably uniform results in all patients. All the drugs used in these conditions do carry some side effects. Anticholinergics produce dry mouth, tachycardia in some patients, are contraindicated in glaucoma and prostatic hypertrophy and other antispasmodic agents may cause drowsiness as a side effect. Analgin is implicated in causing bone marrow depression.

In the comprehensive review of a pharmacological properties of diclofenac (Brogden et al, Drugs 20;24–48 (1980) it has been reported to have anti inflammatory activity, analgesic activity and anti pyretic activity. Conventionally it has been used in clinical condition for rheumatic disorders. Recently it has been reported to be of use in painful non-rheumatic syndromes for example biliary colic, {Grossi et al. Current Therapeutic Research, volume 40, No. 5, (1986)} and acute renal colic {Garcia Alonso F. et al, Eur. J. Clin Pharmacol, 40, 543–546 (1991)}.

However it has been reported that diclofenac sodium intramuscular is more effective than narcotic analgesic like pethidine intramuscular in the management of acute renal colic and has fewer side effects. Based on the market survey among the various products available as antispasmodic one major product is composed of analgin with two spasmolytic agents that is pitofenone hydrochloride and fenpiverinium bromide.

No pharmacological composition has been reported in literature as well as no product is available where an non-steroidal anti-inflammatory drugs such diclofenac and nimesulide is employed in combination with spasmolytic agents.

Our findings as disclosed in this patent application indicate that NSAID including diclofenac and nimesulide when combined with fenpiverinium bromide and pitofenone hydrochloride forms an excellent antispasmodic composition. The inventors after expenditure of considerable time, mental faculties and careful experimentation have surprisingly found that diclofenac potentiates the antispasmodic action of pitofenone hydrochloride and fenpiverinium bromide several times. Further, the safety of the combination has been demonstrated in animal models. Thereafter the efficacy of this combination was established by conducting clinical trials in-human volunteers. The composition when given orally and parenterally is not only clinically effective but is superior to the existing therapeutic agents. It is superior in two ways one it has more effective action and second it has fewer side effects.

Accordingly, it is an object of the present invention to provide a novel antispasmodic composition comprising nonsteroidal antiinflammatory drugs, their salts, their chirally pure forms, isomers and derivatives analogues and adducts thereof and pitofenone hydrochloride and fenpiverinium bromide.

It is a further objective of the present invention to provide a process for the manufacture of a novel anti-spasmodic composition comprising diclofenac and pitofenone hydrochloride and fenpiverinium bromide.

It is a further objective of the invention to provide a novel injectable delivery system for the anti-spasmodic composition.

It is a further objective of the invention to provide an antispasmodic composition which can be taken orally by way of a pediatric suspension, capsule/tablet.

SUMMARY OF THE INVENTION

An anti-spasmodic composition comprising a non-steroidal antiinflammatory drug, their salts, their chirally pure forms, isomers and derivatives analogues and adducts thereof and two drugs pitofenone hydrochloride and fenpiverinium bromide in a pharmaceutically acceptable combination. The composition is capable of being used in an oral and parenteral dosage form.

DETAILED DESCRIPTION OF THE INVENTION

The various non-steroidal antiinflammatory drugs that can be used in the present invention can be divided into two groups—phenylacetic acid derivatives and sulphonanilides. The non-steroidal antiinflammatory drugs that can be used along with pitofenone hydrochloride and fenpiverinium bromide in the present invention are selected from the following group diclofenac, diclofenac sodium, diclofenac potassium, etodolac, flurbiprofen, ibuprofen, indomethacin, ketoprofen, ketrolac tometamol, mefenamic acid, nabumeton, naproxen, naproxen sodium, nimesulide, piroxicam, sulindac, zomiperac sodium, piroxicam cyclodextrin.

In order to see the effect of NSAID on the antispasmodic activity of pitifenone hydrochloride and fenpiverinium bromide an experiment was conducted on standard isolated tissues of experimental animal. The tissue chosen for the experiment was the distal portion of colon of rat. The NSAID selected for the experiment was diclofenac sodium.

The percentage inhibition of acetylcholine-induced contraction (at dosage level of 100 ng/m) was studied with varied concentration of pitofenone hydrochloride in the dose range of 10–80 nano gm/ml.

The experiment was then conducted at the same dose level of acetylcholine and pitofenone hydrochloride but in the presence of diclofenac sodium (dose level 20 μg/ml. The data obtained in the experiment is collected in Table -1. The data clearly indicates that diclofenac shows synergistic (potentiating) action with pitofenone hydrochloride as an antispasmodic when tested on rat colon.

The percentage inhibition of acetylcholine -induced contraction (at dosage level of 100 ng/ml) was studied with varied concentration of fenpiverinium bromide in the dose range of 0.5–2 ng/ml.

The experiment was then conducted at the same dose level of acetylcholine and fenpiverinium bromide but in the presence of diclofenac sodium (dose level 20 μgm/ml). The data obtained in the experiment is collected in Table -2. The data clearly indicates that diclofenac shows synergistic (potentiating) action with fenpiverinium bromide as an antispasmodic when tested on rat colon.

Furthermore, to evaluate the safety of the novel combination of the present invention, sub chronic oral toxicity studies (28 days) were carried out by administration of diclofenac free acid, pitofenone hydrochloride and fenpiverinium bromide to rats. 25 male and 25 female rats were selected for the study. The animals were housed appropriately. They were divided into 5 groups of five male and five female rats each.

Each group received the treatment as indicated below

Classification of Groups

GROUP I: vehicle (water/CMC): 10 ml/kg—(5M & 5F)
GROUP II: diclofenac free acid: 20 mg/kg—(5M & 5F)
GROUP III: pitofenone HCL: 2 mg/kg—(5M & 5F)
GROUP IV: fenpiverinium bromide: 0.04 mg/kg—(5M & 5F)
GROUP V: (5M & 5F)

| | |
|---|---|
| Diclofenac free acid | 20 mg/kg |
| + | + |
| Pitofenone hydrochloride | 2 mg/kg |
| + | + |
| Fenpiverinium bromide: | 0.04 mg/kg |
| Route | Oral |
| Volume of Administration | 1.5–3.5 ml |
| Frequency | Once daily, 6 days a week, |
| Duration | 4 weeks |

The animals were weighed every day and observed for appearance, activity and behavior everyday and body weight every week. No animal died during the study.

At the end of the fourth week all the animals were bled from the heart for biochemical and hematological studies. No abnormalities were seen in any of the test groups when compared with the control. This established the safety of the combination.

Several formulations can be made in the form of tablets or injections comprising the three ingredients diclofenac and like non-steroidal antiinflammatory drugs and their salts, pitofenone hydrochloride and fenpiverinium bromide.

Besides the ingredients disclosed above the composition also comprises the usual excipients like starch, microcrystalline cellulose, DCP, purified talc, magnesium stearate etc. described in the standard text. Tablets may be dispensable or film coated, sugar coated or specially coated as described in the existing art. (Pharmaceutical Dosage forms: Tablets, vol 1–3, Eds., H. A. Lieberman and L. Lachman Dekker New York.)

As disclosed earlier the composition can be employed in the tablet form and in the injection form. The composition of the invention can also be in any form commonly employed for administration i.e. drink solution or suspension, a concentrated drink solution to be diluted before use, solution or suspension encapsulated in soft gelatin capsules, granules, syrups, liquids, suspensions, elixirs, caplets, powders, chewable, waffers, lozenges, solutions freeze dried for oral or injectable dosage forms. The pharmaceutical composition may also contain flavourings, colourings and/or sweeteners.

Such composition can be administered orally or by intramuscular route they can also be administered in form of modified release, sustained release, controlled release, timed release formulations. They can also be administered by ocular, intransal, obuccal, sublingual, transdermal, rectal, vaginal and others related administration routes.

In the tablet form the concentration of the three ingredients are:

Non-steroidal antiinflammatory drugs and their salts— from 6.188 to 61.88% w/w

Pitofenone hydrochloride—from 0.39 to 12.38 w/w

Fenpiverinium bromide—from 0.006 to 1.24% w/w

The tablets may contain specialized ingredients to modify, sustain or control release on one or more ingredients resulting in modified, sustained or controlled release products. (Controlled Drug Delivery Fundamentals and Applications, second edition eds., J. R. Robinson and V. H. Lee, Marcel Dekker, New York.) In the injection form the concentration of the ingredients are Non-steroidal antiinflammatory drugs and their salts— from 1.0 to 10% w/v Pitofenone hydrochloride—from 0.05 to 2.0% w/v Fenpiverinium bromide—from 0.001 to 0.2% w/v The vehicle of the injectable preparation may consists of aqueous, non aqueous or specially formulated amphiphilic base containing suitable stabilizers, antioxidants buffers and other additives. The drug(s) may be dissolved or suspended.

The invention will now be described with reference to the foregoing examples:

EXAMPLE 1

Preparation of Dispersible Antispasmodic Tablets with Diclofenac Free Acid as the NSAID

| S. No. Component | Quantity Per tablet | Quantity for 1.0 Lac tablet |
|---|---|---|
| 1. Diclofenac free acid | 46.5 mg | 4.65 kg |
| 2. Pitofenone hydrochloride | 5.0 mg | 0.5 kg |
| 3. Fenpiverinium bromide | 0.1 mg | 10.0 gm |
| 4. Microcrystalline Cellulose | 203.0 mg | 20.3 kg |
| 5. Aerosil - 200 | 5.0 mg | 0.5 kg |
| 6. *Starch | 50.0 mg | 5.0 kg |
| 7. Povidone | 1.5 mg | 0.150 kg |
| 8. Isopropyl alcohol | ** | 26 lt |
| 9. Magnesium Stearate | 1.0 mg | 0.10 kg |
| 10. Purified Talc | 2.9 mg | 0.29 kg |
| 11. Ac-di sol | 10 mg | 1.0 kg |

* Taken 10% extra to compensate for loss on drying.
** Lost in process.

EXAMPLE 2

Preparation of Antispasmodic Tablets with Diclofenac Sodium as NSAID

| S. No. Component | Quantity Per tablet | Quantity for 1.0 Lac tablet |
|---|---|---|
| 1. Diclofenac sodium | 50.0 mg | 5.0 kg |
| 2. Pitofenone hydrochloride | 5.0 mg | 0.5 kg |
| 3. Fenpiverinium bromide | 0.1 mg | 0.01 kg |
| 4. Microcrystalline cellulose | 23.9 mg | 2.39 kg |
| 5. *Starch | 66.0 mg | 6.6 kg |
| 6. Purified talc | 2.5 mg | 0.25 kg |
| 7. Magnesium stearate | 2.5 mg | 0.15 kg |
| 8. Sodium starch glycollate | 1.5 mg | 0.15 kg |
| 9. Sodium lauryl sulphate | 1.5 mg | 0.15 kg |
| 10. Povidone | 3.0 mg | 0.3 kg |
| 11. Isopropyl alcohol | ** | 5.0 ltr. |

* Taken 10% extra to compensate for loss on drying.

Film Coating Formula

| Hydroxy propyl methyl cellulose | 8.0 mg | 0.800 kg |
|---|---|---|
| PEG 400 | 0.8 mg | 0.08 kg |
| Isopropyl alcohol | ** | 7.5 ltr. |
| Methylene chloride | ** | 15.0 ltr. |
| Purified talc | 1.4 mg | 0.14 kg |
| Titanium dioxide | 1.4 mg | 0.14 kg |

Step 1. All the ingredients were weighed and sieved through a sieve of mesh size 60 (linear inch).

Step 2. Diclofenac sodium (5.0 kg was mixed with microcrystalline cellulose (2.39) and starch (6.6 Kg)

Step 3. Pitofenone hydrochloride (0.5 kg) and fenpiverinium bromide (0.01 kg) are geometrically mixed and then added to the bulk of step 2.

Step 4. A solution of polyvinyl pyrrolidone (0.3 Kg) in isopropyl alcohol (5.0 ltr) was prepared.

Step 5. Granulated the bulk of step 3 with the binder solution (bulk of step 4)

Step 6. The wet mass was passed through sieve no 18 to obtain granules which were dried at a temperature of 45°–50° C. and dry sieved through sieve no 18.

Step 7. Magnesium stearate (0.25 kg), purified talc (0.25 kg) sodium lauryl sulphate (0.15 kg) and sodium starch glycolate (0.15 kg) was passed through sieve of mesh size 60.

Step 8. Mixed the bulk of step 7 with that of step 6.

Step 9. The bulk of step 8 is compressed into tablets in a tablet compression machine at on average weight of 150.0 mg.

Step 10. A film coating solution is passed through colloid mill and the core tablets is coated with it.

EXAMPLE 3

Preparation of Antispasmodic Tablets with Nimesulide as NSAID

| S. No. Component | Quantity Per tablet | Quantity for 1.0 Lac tablet |
|---|---|---|
| 1. Nimesulide | 100 mg | 10 kg |
| 2. Pitofenone Hydrochloride | 5.0 mg | 0.5 g |
| 3. Fenpiverinium bromide | 0.1 mg | 10.0 gm |
| 4. Microcrystalline cellulose | 203.0 mg | 20.3 kg |
| 5. Aerosil | 7.0 mg | 10.6 kg |
| 6. *Starch | 100.0 mg | 10.0 kg |
| 7. Povidone | 2.0 mg | 0.2 kg |
| 8. P. water | ** | 18 lt |
| 9. Magnesium stearate | 1.0 mg | 0.10 kg |
| 10. Pregelatinized starch | 17 mg | 1.7 kg |
| 11. Sodium lauryl sulphate | 1.5 mg | 0.150 kg |
| 12. Chremophor RH 40 | 2.0 mg | 0.2 kg |

* Taken 1 0% extra to compensate for loss on drying.
** Lost in process

EXAMPLE 4

Preparation of Anti Spasmodic Injection with Diclofenac as NSAID

| S. No. Component | Per ml | for 1.0 lac Ampoules |
|---|---|---|
| 1. Diclofenac sodium | 25.0 mg | 7.5 kg |
| 2. Pitofenone hydrochloride | 2.0 mg | 0.6 kg |
| 3. Fenpiverinium bromide | 0.02 mg | 0.006 kg |
| 4. Benzyl alcohol | 5.12 mg | 1.536 kg |
| 5. Propylene glycol | 0.4 ml | 12.0 ltr |
| 6. Sodium sulphite (anhydrous) | 1.0 mg | 0.3 kg |
| 7. *Hydrochloric acid (concentrated) | 0.002 ml | 0.6 ltr |
| 8. D-Mannitol | 5.0 mg | 1.5 kg |
| 9. Disodium edetate | 0.67 mg | 0.201 kg |
| 10. Water for injection | qs to 1.0 ml | qs to 300 ltr. |

* if required
NB 1.0 lac Ampoules = 300 ltr.

Step 1. Benzyl alcohol (1.8 kg) is distilled at 204° to 208° C. The first and last portion is rejected and stored under nitrogen.

Step 2. Diclofenac sodium (7.5 kg) is dissolved in water for injection (75.0 ltr) and warmed, if required.

Step 3. Benzyl alcohol (1.536 kg), is dissolved in propylene glycol (120.0 ltr.)

Step 4. Bulk of step 3 is added to bulk of step 2 and mixed.

Step 5. Pitofenone Hcl (0.6 kg) is dissolved in WFI (3.0 ltr) and added to bulk of step 4 and mixed.

Step 6. Fenpiverinium bromide (0.06 kg) is dissolved in WFI, (1.0 ltr), and added to the bulk of step 5 and mixed.

Step 7. D-mannitol (1.5 kg), sodium sulphite (0.3 kg) and disodium edetate (0.201 kg) is dissolved in WFI (10.0 ltr), added to the bulk of step 6 and mixed.

Step 8. The pH of the bulk of step 7 is adjusted to between 8.2 and 8.8 if required by addition of hydrochloric acid.

Step 9. The volume is made to 300.0 ltr. by the addition of WFI.

Step 10. The bulk is sterilized by filtration using $2\mu$ prefilter and $0.22\mu$ filter under nitrogen.

Step 11. The sterilized liquid is filled in amber coloured ampoules (3.0 ml per ampoule), flushed with nitrogen and sealed using ampoule filling and sealing machine.

NOTE—Step 10 and 11 is carried out in aseptic area.

EXAMPLE 5

Preparation of Anti Spasmodic Injection with Nimesulide as NSAID

| S. No. | Component | Per ml. |
|---|---|---|
| 1. | Nimesulide | 100 mg |
| 2. | Pitofenone hydrochloride | 2.0 mg |
| 3. | Fenpiverinium bromide | 0.2 mg |
| 4. | Benzyl alcohol | 0.04 ml |
| 5. | Benzyl benzoate | 0.76 ml |
| 6. | Dimethylacetamide | 0.2 ml |
| 7. | Ethyl Oleate | q.s 2.0 ml |
| 8. | BHA | 0.002 mg |

TABLE 1

Effect of diclofenac sodium (20 µg/ML) on antispasmodic activity of pitofenone hydrochloride

| Drug | Dose (ng/ml) | Percentage inhibition of Ach (100 ng/ml) -induced contraction | |
|---|---|---|---|
| | | Before diclofenac Na | After diclofenac Na |
| Pitofenone Hcl | 10 | 0 | 100 |
| " | 20 | 0 | 100 |
| " | 40 | 0 | 100 |
| " | 80 | 20.2 | 100 |

TABLE 2

Effect of diclofenac sodium (20 µ/ml) on antispasmodic activity of fenpiverinium bromide

| Drug | Dose (ng/ml) | Percentage inhibition of Ach (100 ng/ml) -induced contraction | |
|---|---|---|---|
| | | Before diclofenac Na | After diclofenac Na |
| Fenpiverinium Bromide | 0.5 | 43.8 | 100 |
| " | 1.0 | 78.7 | 100 |
| " | 2.0 | 100 | 100 |

Clinical Trials

The following patients were included:

Patients in the age group of 16–60 years

Non-pregnant females were also included

Patients with biliary, intestinal and ureteric colic

Patients with any of the above conditions who could not be administered antispasmodic drugs belonging to the anticholinergic group (patients with glaucoma prostatic hypertrophy) were also included.

The following patients were excluded:

Patients with peptic ulcer disease

Patients requiring immediate surgery for their underlying condition were also excluded from the study.

Sample Size: Fifty patients.

Study Procedure: The study was open labeled.

Patients attending the surgical OPD with complaint of moderate to severe abdominal pain and diagnosed to have one of the conditions listed in the inclusion criteria were enrolled. According to the study protocol, patients could be hospitalized for the acute condition for observation, and parenteral drug to relieve the acute pain was permitted. If on observation for a few hours, the patient is relieved of the pain but requires oral medication for continued relief of pain after discharge from the ward, the patient was put on test medication if the patient qualified the inclusion criteria.

ADMINISTRATION OF THE TEST DRUG

The test drug was administered orally. The dose was one tablet three times daily for a maximum period of five days. Patients administered the test drug were kept in the emergency ward for observation till such time the patient was relieved of the symptoms.

The protocol permitted patients to receive parenteral antispasmodic in cases of severe and disabling colic. Such patients were discharged on the oral test drug given in the dose of one tablet thrice daily for a maximum period of five days.

CONCOMITANT MEDICATION AND DIETARY ADVICE

Concomitant medication such as antibiotics, urinary antiseptics, medical therapy for gall stones, etc. were continued during the protocol therapy. Similarly, any specific dietary restrictions/advice were also continued.

Patients were not permitted any concomitant antispasmodic therapy during the trial.

ESCAPE MEDICATION AND TERMINATION OF PROTOCOL THERAPY

Patients not responding to the test medication within a period of two (2) hours were administered parenteral analgesic. Such patients were deemed treated and not replaced by fresh patients.

All patients on enrollment were subjected to history, clinical examination and history of past drug therapy which included:
1. Duration of illness
2. Severity of pain
3. Frequency of antispasmodic drug intake
4. Duration of antispasmodic drug use
5. Relief with existing therapy; excellent, good, fair poor
6. Need to take parenteral antispasmodic while on existing oral therapy
7. Side effects with current therapy

EVALUATION PARAMETERS

The following parameters were used to determine the efficacy and safety of the test medication.
1. Did the patient receive parenteral antispasmodic prior to oral therapy with the test drug.
2. Severity of pain after the first dose
3. Speed of relief
4. Did the patient need parenteral drug for pain relief after administration of the first dose of the test drug
5. Severity of pain at home after subsequent doses
6. Duration of intake of test drug
7. Patient's evaluation of the test drug
8. Investigator's evaluation of the test drug

FINAL EVALUATION

EXCELLENT: Acute pain relieved in less than half an hour. Parental drug for pain relief not needed. Drug well tolerated without any side effects.

GOOD: Acute pain relieved in one to two hours without any need for parenteral drug for pain relief. Drug well tolerated without any side effects.

POOR: Drug not effective in relieving pain. Parental drug required to control symptoms.

RESULTS

Total number of patients enrolled: 50
Number of patients completing the study: 50

DIAGNOSTIC BREAKUP OF PATIENTS ENROLLED

| DIAGNOSIS | NUMBER | MALE | FEMALE |
|---|---|---|---|
| Intestinal colic | 23 | 11 | 12 |
| Ureteric colic | 19 | 12 | 7 |
| Biliary colic | 8 | 0 | 8 |
| Total | 50 | 23 | 27 |

MEAN AGE OF PATIENTS—YEARS

Males 33.5
Females 40.6

DURATION OF ILLNESS—Years

| DIAGNOSIS | MALES | FEMALES |
|---|---|---|
| Intestinal colic (n = 23) | 5.8 (11) | 6.9 (12) |
| Ureteric colic (n = 19) | 6.8 (12) | 7.2 (7) |
| Biliary colic (n = 8) | (0) | 7.3 (8) |

DURATION OF ANTISPASMODIC DRUG USE—Years

| DIAGNOSIS | MALES | FEMALES |
|---|---|---|
| Intestinal colic | 5.1 | 6.4 |
| Ureteric colic | 6.0 | 7.0 |
| Biliary colic |  | 6.8 |

FREQUENCY OF ANTISPASMODIC DRUG INTAKE

Tablets/week

| DIAGNOSIS | MALES | FEMALES |
|---|---|---|
| Intestinal colic | 6 | 10 |
| Ureteric colic | 7 | 12* |
| Biliary colic |  | 15 |

*$p < 0.05$

From the above tables of demographic details, there is no statistically significant difference between the two sexes with relation to age, diagnosis and duration of illness. However, there is a statistically significant difference in the mean number of tablets per week consumed for the relief of ureteric colic for female patients in comparison to males (p, 0.05). Since there were no male patients with biliary colic, it is not possible to determine the difference between the two sexes.

Past History of Parenteral Antispasmodic Drug Intake

Almost all patients needed parenteral antispasmodic drugs for symptomatic relief while on oral antispasmodic drugs. Although all patients were not able to exactly remember, the frequency of parenteral antispasmodic drug therapy varied from once every one month to two to four times every month.

Most of the patients of both sexes reported uniformly good response with existing antispasmodic drug therapy. Five patients of intestinal colic, three of ureteric colic and two of biliary colic reported uncomfortable side effect such as, dry mouth and palpitations with anticholinergic drugs.

Need for additional parenteral antispasmodic drug in the present study: No patient required parenteral antispasmodic drug in the present study.

INTENSITY OF PAIN AFTER THE FIRST DOSE (As Measured on Visual Analogue Scale 0–100 mm)

Intensity of Pain

|  | 30 minutes | 1 hour | 2 hours |
|---|---|---|---|
| Intestinal colic | 55 | 23* | 12* |
| Ureteric colic | 64 | 22* | 13* |
| Biliary colic | 70 | 25* | 17* |

*$p < 0.05$
**$p < 0.01$

There was a statistically significant reduction in the intensity of pain in all groups of patients at the end of one hour of the first dose. This indicates that the onset of action of diclofenac-pitofenone and fenpiverinium starts within this time period.

DRUG OF HOSPITALIZATION—HOURS

Diagnosis Duration

| Intestinal colic | 2.8 |
|---|---|
| Ureteric colic | 3.9 |
| Biliary colic | 4.3 |

INTENSITY OF PAIN AT THE TIME OF DISCHARGE

Diagnosis Intensity of Pain

| Intestinal colic | 7.75** |
|---|---|
| Ureteric colic | 8.25** |
| Biliary colic | 9.12** |

**$p < 0.001$

There was statistically highly significant reduction of pain at the time of discharge as measured by the visual analogue scale.

INTENSITY OF PAIN DAY 2–5

(As Measured by Visual Analogue Scale 0–100 mm)

Intensity of Pain Day 2–5

| DIAGNOSIS | DAY 2 | DAY 3 | DAY 4 | DAY 5 |
|---|---|---|---|---|
| Intestinal colic | 1.2** | 0 | 0 | 0 |
| Ureteric colic | 2.1** | 0 | 0 | 0 |
| Biliary colic | 3.2** | 1.3 | 0 | 0 |

**$p < 0.001$

All patients had practically no pain from day 2 onwards as measured by the visual analogue scale. All patients had the last dose of the test drug at approximately 8 p.m. on day 1. This indicates that the duration of action of the test antispasmodic is more than 8 hours.

INTAKE OF TEST ANTISPASMODIC—DAY 1 TO DAY 5

Number of Tablets Per Day

| DIAGNOSIS | DAY 1 | DAY 2 | DAY 3 | DAY 4 | DAY 5 |
|---|---|---|---|---|---|
| Intestinal colic | 3 | 2 | 1 | 0 | 0 |
| Ureteric colic | 3 | 2 | 1 | 0 | 0 |
| Biliary colic | 3 | 2 | 2 | 1 | 0 |

All the patients irrespective of diagnosis took three tablets on day 1 and 2 tablets on day 2. However, on day 3 patients of intestinal and ureteric colic took 1 tablet and did not take any tablets on days 4 and 5 while patients of biliary colic continued to take 2 tablets on days 2 and 3 and one tablet on day 4. On day 5 patients of biliary colic did not need any medication.

Patients were instructed to bring the container along with the unconsumed tablets to the clinic on day 5 to determine the number of tablets the patients actually consumed after discharge from the hospital.

EVALUATION OF THE TEST DRUG BY THE PATIENT

| | |
|---|---|
| Worse than previous therapy | NIL |
| Same as previous therapy | 24 |
| Better than previous therapy | 22 |
| Markedly better than previous therapy | 4 |

EVALUATION OF THE TEST DRUG BY THE INVESTIGATOR

| | |
|---|---|
| EXCELLENT (Relief of pain <30 minutes | 3 |
| GOOD (Relief on pain in 1–2 hours | 47 |

Side effects: No side effects observed in any patient.

OBSERVATIONS AND COMMENTS: The combination of diclofenac+pitofenone and fenpiverinium produced good results in patients of intestinal, ureteric and biliary colic in both sexes in the present open labeled study without any side effects.

We claim:

1. An anti-spasmodic composition comprising a combination of pitofenone hydrochloride and fenpiverinium bromide, and an anti-spasmodic enhancing effective amount of diclofenac free acid or its salts.

2. The composition as claimed in claim 1 wherein said salt of diclofenac is sodium or potassium.

3. The composition as claimed in claim 1 wherein diclofenac is present as the salt of sodium.

4. The composition as claimed in claim 1 wherein the composition is in the form of a tablet.

5. The composition as claimed in claim 4 wherein the ingredients are present in the following proportions:

diclofenac free acid or its salts—From 6.188 to 61.88% w/w

Pitofenone hydrochloride—From 0.39 to 12.38% w/w

Fenpiverinium bromide—From 0.006 to 1.24% w/w.

6. The composition as claimed in claim 4 wherein the composition also comprises ingredients to modify, sustain or control release of one or more ingredients resulting in modified, sustained or controlled release products.

7. The composition as claimed in claim 1 wherein the said composition is in injectable form.

8. A composition as claimed in claim 7 wherein the said composition has the ingredients in the following proportions:

diclofenac free acid or its salts—From 1.0 to 10% w/v

Pitofenone hydrochloride—From 0.05 to 2.0% w/v

Fenpiverinium bromide—From 0.001 to 0.2% w/v.

9. The composition as claimed in claim 1 wherein it is in the form selected from the group consisting of a drink solution, a concentrated drink solution to be diluted before use, solution encapsulated in soft gelatin capsules, the solution freeze dried for oral or injectable dosage forms, granules and controlled drug delivery systems, syrups, suspensions, elixirs, caplets, powders, chewable, waffers and lozenges.

10. The composition as claimed in claim 1 which comprises flavourings, colourings and/or sweetners.

* * * * *